United States Patent [19]

Goetzl et al.

[11] 4,021,387

[45] May 3, 1977

[54] EOSINOPHILOTACTIC TETRAPEPTIDES

[75] Inventors: Edward J. Goetzl; K. Frank Austen, both of Boston, Mass.

[73] Assignee: President and Fellows of Harvard College, Cambridge, Mass.

[22] Filed: Nov. 19, 1975

[21] Appl. No.: 633,467

[52] U.S. Cl. .................................. 260/8; 260/6; 260/112.5 R; 424/177
[51] Int. Cl.² ................. C07C 103/52; C08H 1/00
[58] Field of Search ..................... 260/112.5 R, 6, 8

[56] References Cited
OTHER PUBLICATIONS

Kay et al., J. Exp. Med., 133, 602–619 (1971).
J. M. Stewart and J. D. Young, "Solid Phase Peptide Synthesis," Freeman and Co., San Francisco, 1969, pp. 9–13.

*Primary Examiner*—Lewis Gotts
*Assistant Examiner*—Reginald J. Suyat

[57] ABSTRACT

Two eosinophilotactic tetrapeptides of amino acid sequence Val-Gly-Ser-Glu and Ala-Gly-Ser-Glu have been isolated from extracts of human lung fragments. These tetrapeptides have been synthesized by solid phase peptide synthesis procedures and the synthetic and natural materials behaved similarly in analytical assays and bioassays. Novel N-terminal analogs have been prepared and have shown eosinophilotactic activity. Thus, the tetrapeptides disclosed herein have utility as therapeutic agents in the prophylaxis and/or treatment of parasitic diseases, anaphylaxis and bronchial asthma.

9 Claims, No Drawings

EOSINOPHILOTACTIC TETRAPEPTIDES

The invention described herein was made in the course of work under a grant or award from the Department of Health, Education and Welfare.

BACKGROUND OF THE INVENTION

The eosinophil chemotactic factor of anaphylaxis (ECF-A) was discovered in 1971 as a mediator released during immediate hypersensitivity reactions in guinea pig (Kay et al., J. Exp. Med. 133, 602 [1971]) and human (Kay and Austen, J. Immunol. 107, 399 [1971]) lung slices. ECF-A was subsequently recognized to be present totally preformed in rat mast cells in association with the granules (Wasserman et al., J. Immunol. 112, 351 [1974]), human leukemic basophils (Lewis et al., J. Immunol. 114, 87 [1975]) and mast cell-rich tissues such as human lung and nasal polyps (Kaliner et al., New Eng. J. Med. 289, 277 [1973]).

The activities of ECF-A are preferentially directed to eosinophils as compared to neutrophil and mononuclear leukocytes and include chemotaxis, chemotactic deactivation, stimulation of the hexose monophosphate shunt and release of granular enzymes.

Due to the fact that only extremely small quantities of ECF-A are present either preformed or after release from sensitized tissue, it has not heretofore been possible to purify sufficient material for structural characterization. Moreover, since partially purified preparations of ECF-A contain histamine and other peptidic materials which produce other pharmacological effects, it has not been possible to accurately assess the spectrum of activities or potency of ECF-A or to employ this material as a therapeutic agent.

DESCRIPTION OF THE INVENTION

The present invention relates to the purification, characterization and synthesis of two eosinophilotactic tetrapeptides. Isolation of these tetrapeptides from extracts of human lung fragments has been accomplished by sequential purification on Sephadex G-25, Dowex-1, Sephadex G-10 and paper chromatography. The amino acid sequence for these compounds has been determined as Val-Gly-Ser-Glu and Ala-Gly-Ser-Glu. Chemotactic activity is dependent on both the $NH_2$-terminal and the COOH-terminal residues. Both tetrapeptides can be conveniently synthesized using conventional peptide synthesis procedures, more preferably utilizing solid phase peptide synthesis. Both natural and synthetic tetrapeptides, when in the form of pure compounds essentially free of other biogenic peptides and histamine in accordance with the present invention, are preferentially chemotactic for eosinophils and render them unresponsive to a subsequent stimulus.

A further aspect of the present invention relates to the synthesis of analogs of the aforesaid two natural tetrapeptides. This class of novel compounds is represented by the formula X-Gly-Ser-Glu            I' wherein X is selected from the group consisting of

| Amino Acids | |
|---|---|
| Ile | N-formyl Met |
| Tyr | Try |
| Cys | Leu |
| Met | Phe |
| | Other Groups |
| Hexanoyl | Caproyl |
| Valeryl | Isocaproyl |
| Isovaleryl | |

Compounds of formula I' are readily prepared by utilizing conventional peptide syntheses. Suitable syntheses include the homogeneous phase syntheses where the reagents and the growing peptide fragement are all dissolved in a solvent system or more preferably, solid phase syntheses where the growing peptide chain is coupled to an insoluble polymer and soluble reagents are added sequentially in a series of heterogeneous reactions. As these various procedures are notorious in the art, it is not believed necessary to describe them in great detail.

In a preferred embodiment of the process aspect of the present invention a solid phase synthesis is employed. As a first step in such procedure a polymeric resin having suitable reactive groups is reacted with a N-protected glutamic acid ester, preferably as its cesium salt.

Examples of suitable polymeric resins useful in the practice of this process aspect include those described by Merrifield in Adv. Enzymol., 32, 221 (1969). A preferred resin described therein is chloromethylated copolystyrenedivinylbenzene. Other reactive group modified resins may also be employed such as bromoacyl resin, benzhydryl resin, 4-methylthiophenyl resin, 4-hydrazinobenzoyl resin, t-alkylalcohol resin, p-oxobenzyl alcohol resin, p-oxy-benzyloxycarbonylhydrazide resin 3-nitro-4-bromoethyl-benzoylamide resin, halo alpha-methyl phenacyl resin and the like.

Protection of the terminal amino group during the synthesis is readily accomplished utilizing a conventional terminal amino protecting group. When a solid phase synthesis is employed, the terminal amino protecting group will be one conventionally used for that purpose.

Suitable protecting groups for the terminal amino group during the synthesis include, for example, carbobenzoxy, p-nitrobenzyloxycarbonyl, p-chlorobenzyloxycarbonyl, p-bromobenzyloxycarbonyl, diisopropyloxycarbonyl, p-toluenesulfonyl, formyl, phthaloyl, 2-(p-biphenyl)isopropyloxycarbonyl, trifluoroacetyl, arylphosphoryl, alkylphosphoryl, phenylsulfonyl, benzylsulfonyl, tritylsulphenyl, o-nitrophenylsulphenyl, γ-chlorobutynyl, o-nitrophenoxyacetyl, trityl, benzyl, p-methoxycarbobenzoyl, tolyloxycarbonyl, allyloxycarbonyl, cyclopentyloxycarbonyl, t-butyloxycarbonyl, 1,1-dimethylpropoxycarbonyl and the like. For use in solid phase synthesis, the t-butyloxycarbonyl (BOC) protecting group is especially preferred.

Ester derivatives of N-protected glutamic acid useful in protecting the free carboxy moiety includes the benzyl and p-nitro-benzyl esters. These groups are stable to the deprotecting conditions for freeing the terminal amino group but are cleaved under the conditions used to cleave the peptide-resin bond.

In general, a molar excess of the protected amino acid will be employed. Preferably a two-fold molar excess is used.

The N-protected glutamic acid-resin composition is then treated to selectively remove the N-protecting group without affecting the amino acid-resin bond utilizing procedures well known in the art for the particular protective group and resin involved. Thus, when the protective group is t-butyloxycarbonyl and the resin is copolystyrene-divinyl benzene, deprotection is readily accomplished by treatment with trifluoroacetic acid.

In the next step in the synthesis the second amino acid, serine bearing protective groups on the amino and hydroxy groups, is coupled to the free amino group on the glutamic acid-resin composition utilizing a coupling agent to facilitate formation of the peptide bond. Preferred coupling agents for this purpose include the carbodiimides such as dicyclohexylcarbodiimide (DCC). A molar excess of the protected amino acid is also used in this step. Preferably, a three-fold excess is used.

Protective groups for the hydroxy function of serine are well known in the art. Preferably such groups will be removable under the acidic conditions employed to cleave the peptide-resin bond, but will be resistant to cleavage under the deprotecting conditions employed herein. Preferred hydroxy protective groups for serine are ethers formed with the benzyl or p-nitrobenzyl groups.

The third amino acid component may then be added after deprotection of the terminal amino group. Addition of N-protected glycine, preferably BOC-Gly, to the resulting dipeptide-resin composition of the formula

$$H_2N-Ser(OR^1)-Glu(OR^2)-\text{®} \qquad I$$

wherein $R^1$ and $R^2$ each independently is selected from benzyl and p-nitrobenzyl and ® is a conventional solid phase peptide synthesis resin is carried out in the same manner as described above for the addition of serine to produce a tripeptide-resin composition of the formula

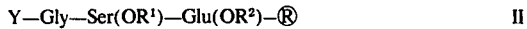

$$Y-Gly-Ser(OR^1)-Glu(OR^2)-\text{®} \qquad II$$

wherein Y is a conventional solid phase peptide synthesis N-terminal amino protecting group and $R^1$, $R^2$ and ® are as above.

The composition of formula II may then be employed, after deprotection, to produce tetrapeptide-resin compositions of the formula

$$Y-X^1-Gly-Ser(OR^1)-Glu(OR^2)-\text{®} \qquad III$$

wherein $X^1$ is Val, Ala or X and X, Y, $R^1$, $R^2$ and ® are as above.

Removal of the protected tetrapeptide from the resin can be accomplished in a manner know per se. The conditions and reagents employed will of course depend on the nature of the resin, the linking group and the protective groups utilized. Thus, for example, if the resin is chloromethylated copolystyrenedivinylbenzene, the linking group benzyl ester and the protecting groups are t-butyloxycarbonyl and O-benzyl, then cleavage of the tetrapeptide from the resin with concomitant removal of the protecting groups is readily accomplished by treatment with HBr-trifluoroacetic acid. There is obtained in this manner the compounds of the present invention having the following formula:

$$X^1\text{-Gly-Ser-Glu} \qquad IV$$

wherein $X^1$ is as above.

The synthetic tetrapeptides described above have eosinophil chemotactic and deactivating activity and specificity comparable to that of natural ECF-A. Purified ECF-A preparations were active at 0,6-0.7 nmole per chamber, and $10^{-6}$ M synthetic tetrapeptides which provide 1 nmole per chamber gave similar activity. Purification of the synthetic peptides and extracted ECF-A revealed that the peptide peaks and eosinophilotactic activity had the same characteristics on Dowex-1, Sephadex G-10, paper electrophoresis and paper chormatography.

Inactivation of ECF-A and the synthetic tetrapeptides' eosinophil chemotatic activity by limited digestion with aminopeptidase M reveals that the $NH_2$-terminal sequence is critical to ECF-A activity. This conclusion is supported by the marginal activity of the COOH-terminal tripeptide. The COOH-terminal glutamic residue is also necessary since carboxypeptidase-A digestion reduces the chemotactic action of ECF-A. The ninhydrin positivity of eosinophil chemotactic peaks during ECF-A purification, the susceptibility to aminopeptidase M digestion and the reactivity on dansylation of the $NH_2$-terminus provide evidence that ECF-A has a free $NH_2$-terminus.

The tetrapeptides of formula IV are useful as therapeutic agents in the prophylaxis and/or treatment of parasitic infectious diseases such as schistosomiasis, or allergic manifestations such as anaphylaxis and bronchial asthma. The dosage of compounds of formula IV employed should be regulated according to the individual requirements and dosage form employed and thus can vary between 0.01 to 0.6 $\mu$g/kg per single dose which may be administered one or more times per day.

The compounds of formula IV can be administered in the form of the free acid or as pharmaceutically acceptable non-toxic salts with organic or inorganic acids or bases. Among the acids which the compounds of formula IV form pharmaceutically acceptable acid addition salts are included hydrochloric acid, hydrobromic acid, sulfuric acid, phosphoric acid, citric acid, acetic acid, succinic acid, maleic acid, methane sulfonic acid, p-toluene sulfonic acid and the like. The pharmaceutically acceptable basic salts of the compounds of formula IV include the alkali metal salts such as sodium or potassium or the alkaline earth metal salts such as calcium.

The tetrapeptides of the invention can be administered alone or in the form of pharmaceutical preparations suitable, for example, for parenteral, enteral or intranasal administration. For the preparation of pharmaceutical preparations, the tetrapeptides can be compounded with inorganic or organic substances which are inert and physiologically acceptable. Examples of such adjuvants are:

for injection solutions: water, alcohols, glycerin and vegetable oils;

for suppositories: natural and hydrogenated oils and waxes;

for intranasal or endobronchial aerosol sprays: water, glycerin and other liquid substances which are tolerated by the mucous membrane or micro-size powders suitable for solid inhalation.

The pharmaceutical preparations can also contain, for example, preservatives, stabilizers, wetting agents and buffers.

All amino acids having an asymmetric carbon atom have the 1-configuration.

EXAMPLE 1

ECF-A Purification

Human lung surgical specimens were processed to fragments in 100 g. lots as described by Orange et al., J. Exp. Med. 134, 136–148 (1971) and extracted twice with 100 ml. of either butanol:glacial acetic acid (10:1) or alkaline Tyrode's buffer —0.05 M Tris (pH 8.2) by homogenization with a tissue grinder and sonication for 15 minutes at 4° C. The extracts were centrifuged in 40 ml. portions to obtain a clear supernatant fraction. Lung fragments, passively sensitized with IgE-rich serum from a ragweed-sensitive individual and challenged with antigen E (Orange et al., J. Exp. Med. 134, 136–148 [1971]) were employed as a source of immunologically released ECF-A. Both the extracted and immunologically released ECF-A were applied to a Sephadex G-25 column equilibrated and eluted with 0.01 N acetic acid for the extracts and Hanks' salt solution for the immunologically released material. Descending Sephadex G-25 and G-10 gel filtration were carried out with a capillary pump producing flow rates of 3–4% of bed volume per hour at 4° C. Dowex AG-1 ion exchange chromatography employed a linear gradient of −0.3 pH units per 4 bed volumes in the pH range from 5 to 2. High voltage paper electrophoresis was performed on a horizontal electrophoresis apparatus equipped with an aluminum cooling plate and operated at 50 volts per cm at 10° C. employing 0.05 M pyridine-acetate pH 7.4 buffer. Descending paper chromatography was performed with a chromatocab A-125 utilizing the organic layer of a mixture of water:butanol:acetic acid (5:4:1). All papers were prewashed for 24 hours with the appropriate solvents. Strips of paper 2 cm wide were eluted with 34 ml. of 0.01 N $NH_4OH$, and the samples were relyophilized twice from 2 ml. distilled water. Ninhydrin determination of portions of eluates from Dowex-1 or paper followed a standard method (Rosen, Arch. Biochem. Biophys, 67, 10–17 [1957]).

The extraction of human lung fragments with either acidic-butanol or alkaline Tyrode's buffer yielded large quantities of eosinophil chemotactic activity with a range of 4 samples of 710–1080 net eosinophils/hpf/g of lung tissue with acidicbutanol and 420–760 net eosinophils/hpf/g of lung with alkaline Tyrode's buffer. Sephadex G-25 gel filtration of extracts obtained by either procedure revealed considerable heterogeneity in molecular size of the eosinophil chemotactic activity. The major peak of activity of approximate molecular weight 300-1000 coincided with the peak of preferential eosinophil chemotactic activity released by IgE-mediated reactions. Extraction of lung tissue with an acidic aqueous solution (0.1 N acetic acid) or a basic organic solvent system (butanol-pyridine, 10:1 v/v, pH 9.0) gave less than one-half the activity obtained with the aforementioned two solvents, a result consistent with the acidic nature of the active peptides as previously appreciated by electrophoresis. The 3000–1000 molecular weight peak of eosinophil chemotactic activity recovered from Sephadex G-25 was therefore purified by anion exchange chromatography on Dowex-1, where the bulk of the ECF-A eluted in a broad peak at pH 3.0–2.2. The activities eluting at pH 3.0–2.6 and pH 2.6–2.2 were separately pooled and filtered on Sephadex G-10. The single peaks obtained were then subjected to descending paper chromatography. The eosinophilotactic activity chromatographed on paper in a broad area with an Rf relative to DNP-glutamic acid of 0.5–0.7. The majority of the ECF-A in the acidic pool from Dowex-1 traveled further, reflecting greater hydrophobicity. The peak activities eluted from paper chromatography at 10–12 cm and 12–14 cm from both Dowex pools were recombined and subjected to high voltage paper electrophoresis. Two discrete peaks were separated by 2–4 cm at 3 hours; separate analyses indicated that the more hydrophobic peak on paper chromatography was more anodal on high voltage electrophoresis. ECF-A released immunologically from human lung tissue also contained two peaks on either paper chromatography or electrophoresis identical to those from the extract. The material obtained from paper chromatography showed no lipid staining with Rhodamine 6-G.

EXAMPLE 2

Amino Acid Analysis and Sequence Determination amino acid analyses were done according to the method of Spackman et al., Anal. Chem. 30, 1190 (1958) with a Beckman Model 120C automatic amino acid analyzer which demonstrates a precision of ±3% in the 2–10 nmole range. Peptides were hydrolyzed with 0.25 ml. of 6 N HCl in sealed evacuated tubes at 105° C. for 30 hours. Prior performic acid oxidation or the addition of phenol was utilized to seek sulfur-containing amino acids and tyrosine, respectively.

The amino acid sequence of purified peptides was analyzed by dansylation of the amino-terminal residue of a portion of each specimen with DNS-chloride according to the method of Gray, Methods Enzymol. XI, 469 (1967) and Edman degradation of the remainder of the sample to expose the next amino acid for dansylation. Dansyl-peptides were hydrolyzed with 6 N HCl in 5 × 50 mm tubes flushed with $N_2$ and sealed and the DNS-amino acids were identified by twodimensional chromatography on polyamide sheets. Sequential Edman degradation and dansylation were carried out until either the quantity of DNS-amino acid was too small for identification or multiple DNS-amino acids were seen. Sequence analysis from the COOH-terminus was conducted by either hydrazinolysis or carboxypeptidase A digestion with identification of the amino acids liberated with the Beckman amino acid analyzer. Selective tritiation of the COOH-terminal residue followed by hydrolysis and electrophoretic identification of the labeled amino acid was also employed.

Compositional analysis of ECF-A purified by Sephadex G-25, Sephadex G-10 and descending paper chromatography gave a total recovery of 3.0–9.9 nmoles of peptide in each of the 2 peaks on 6 consecutive purifications, representing an overall yield of 3.6–12.2% of the low molecular weight eosinophil chemotactic activity. The mean residue values were low for serine, attributable to losses during acid hydrolysis and for alanine and valine due to cross-contamination of peptides with these two $NH_2$-terminal residues. No basic amino acids were encountered and the only other residues noted in the analyses of both peptides were aspartic acid and leucine with mean residue values ±1 S.D. of 0.19 ±0.23 and 0.27 ±0.32, respectively; these amino acids were not noted after high voltage electrophoresis. Glutamic acid was recognized by total enzymatic digestion of the peptides ruling against the presence of glutamine.

The amino acid sequence of the ECF-A peptides was surmised from a composite of data obtained with half the material from the six preparations. The limited supply and low yields prevented identification of the COOH-terminal residue by sequential Edman-Dansyl processing or concurrent analysis of the NH$_2$-terminal and COOH-terminal residues for any one preparation of peptides. Aminopeptidase M digestion of a preparation of the more acidic pool of ECF-A with 10 μg of enzyme for 2 hours at 37° C. released an average of 0.9 nmoles of alanine and 2.7 nmoles of valine representing a 92% recovery of the NH$_2$-terminal residue in the composition while reducing the eosinophil chemotactic activity by 77%. Carboxypeptidase A digestion of the preparation of ECF-A with 10 μg of enzyme for 2 hours at 37° C. released an average of 3.4 nmoles of glutamic acid representing an 87% recovery of COOH-terminal residue in the composition with a concomitant 65% loss of eosinophil chemotactic activity. Treatment of 4 of the above samples and 5 additional preparations of highly purified ECF-A with periodic acid had no effect.

EXAMPLE 3

Peptide Synthesis

Three grams of chloromethylated copolystyrene-divinylbenzene resin (0.89 mmole of chloride per g.) were reacted with a two-fold molar excess of the cesium salt of BOC-Glu-O-benzyl ester, and then BOC-Ser-O-benzyl ester and BOC-Gly were successively coupled to each deprotected NH$_2$-terminus employing a three-fold molar excess of the next BOC-amino and acid and dicyclohexylcarbodiimide in CH$_2$C$_2$. Each cycle was performed according to known procedures (Stewart and Young, *Solid Phase Peptide Synthesis*, W.H. Freeman and Co., San Francisco, 1969) except that the coupling reaction was carried out for 12 hours, the deprotection reaction employed 25% (v/v) trifluoroacetic acid-CH$_2$Cl$_2$ for 30 minutes and the washing after deprotection consisted of 33% dioxane in CH$_2$Cl$_2$ in alternate washes with CH$_2$Cl$_2$. The completeness of deprotection and coupling was assessed by determination of total resin-free amine with chloride titrations. The 2.15 mmol of BOC-Gly-Ser-Glu-resin synthesized was divided into three equal portions of which one was coupled with BOC-Val, one with BOC-Ala and one left unreacted, after which each was cleaved from the resin with HBr-trifluoroacetic acid. The peptides were freed of volatile contaminants by stepwise evaporation from CH$_2$Cl$_2$, ethanol, 0.1 N acetic acid and water, purified on Sephadex G-10 in 0.01 N NH$_4$OH and on Dowex-1 as for ECF-A, and analyzed for amino acid composition.

The valine and alanine tetrapeptides and their common COOH-terminal tripeptide were synthesized and then purified by the same procedures used for natural ECF-A with the omission of the initial Sephadex G-25 step. The valylpeptide was more acidic than the alanylpeptide on Dowex 1 and paper electrophoresis, and exhibited greater hydrophobicity on paper chromatography. Both peptides co-chromatographed on Sephadex G-10, Dowex-1 and paper, and co-electrophoreses on paper in the same region as natural ECF-A when assessed functionally. Both tetrapeptides were chemotactic for human eosinophils with maximum activity in the $10^{-6}$ to $10^{-7}$ M range, whereas the tripeptide was marginally active. The presence of an equal concentration of peptides on both sides of the filter eliminated the eosinophilotactic response.

EXAMPLE 4

Preferential Eosinophil Chemotactic Activity of Purified ECF-A and Synthetic Peptides When the concentrations of chemotactic factors were standardized to comparable neutrophil chemotactic activity, ECF-A purified from lung extracts and synthetic valyl- and alanyl-tetrapeptides demonstrated preferential eosinophil chemotactic activity relative to the other chemotactic factors as seen in Table 1 below.

TABLE 1

| Preferential Eosinophil Chemotactic Activity of Purified ECF-A and Synthetic Peptides | | | | | | |
|---|---|---|---|---|---|---|
| | | ECF-A | Alanyl-tetrapeptide | Valyl-tetrapeptide | Kallikrein | C5a |
| Neutrophils | Chemotaxis (net leukocytes/hpf) | 69 | 72 | 74 | 67 | 74 |
| | Deactivation (%) | 86 | 100 | 96 | 100 | 79 |
| Eosinophils | Chemotaxis (net leukocytes/hpf) | 96 | 84 | 97 | 13 | 67 |
| | Deactivation (%) | 91 | 92 | 100 | 34 | 77 |
| Mononuclear leukocytes | Chemotaxis (net leukocytes/hpf) | 15 | 18 | 16 | 14 | 72 |
| | Deactivation (%) | 71 | 52 | 67 | 38 | 91 |

Enriched preparations of 95% neutrophils, 69% eosinophils and mononuclear leukocytes, 17% monocytes and 72% lymphocytes were employed. The concentrations of principles for chemotaxis and deactivation were: ECF-A, $10^{-6}$ M; alanyl peptide, $10^{-6}$ M; valyl peptide, $5 \times 10^{-7}$ M; kallikrein capable of generating 65 ng of bradykinin from 0.2 ml. of heated plasma and C5a produced by tryptic digestion of 5 μg purified human C5 per chamber (7). The stimuli for deactivated leukocytes were kallikrein for neutrophils, ECF-A for eosinophils and C5a for mononuclear leukocytes at the same concentrations as above.

Plasma kallikrein exhibited preferential neutrophil chemotactic activity while C5a was equally chemotactic for all three types of leukocytes. Deactivation assessed by residual responsiveness of leukocytes to their preferential chemotactic stimulus showed a similar extent of neutrophil deactivation of all factors consistent with their introduction at comparable neutrophil chemotactic doses. Purified ECF-A and synthetic alanyl- and valyl-tetrapeptides were chemotactic for neutrophils when they were the predominant leukocyte in the test population, and were capable of chemotactically deactivating neutrophils and monocytes as well as eosinophils when the pools of target leukocytes are enriched appropriately (Table 1). Although selectivity of ECF-A for leukocyte deactivation was not demonstrated at the concentrations depicted in Table 1, preferential activity was apparent at a $10^{-8}$ M level where deactivation of neutrophils, eosinophils and mononuclear leukocytes respectively was 62%, 91% and 48% for ECF-A; 49%, 88% and 36% for alanyl-tetrapeptide; and 67%, 95% and 53% for valyl-tetrapeptide.

EXAMPLE 5

Chemotaxis

Blood from normal subjects or patients with peripheral blood hypereosinophilia of 20-95% was incubated for 45 minutes at 37° C. with citrate anticoagulant and dextran to sediment the erythrocytes. The leukocyte-rich supernatant plasma was removed and centrifuged at 100 × g. for 10 minutes at room temperature. The leukocyte pellet was either washed and suspended in Medium 199 made 0.4% in ovalbumin and 0.01 M in Tris pH 7.4 (Medium 199-ovalbumin) and used directly in the chemotactic assays or was employed as a source of specific leukocyte population. Eosinophils were enriched by centrifugation on metrizoate cushions and neutrophils and mononuclear leukocytes were purified by centrifugation on Ficoll-Hypaque cushions, then washed and resuspended in Medium 199-ovalbumin. Chemotaxis was assessed by a modification of the Boyden micropore filter technique. One ml. of cell suspension in Medium 199-ovalbumin containing $3.5 \pm 0.5 \times 10^6$ eosinophils, $2.5 \pm 0.5 \times 10^6$ neutrophils, or $3.0 \pm 0.5 \times 10^6$ mononuclear leukocytes was introduced into each polystyrene disposable chemotactic chamber, fitted with a 3 $\mu$m pore filter for assessment of eosinophil and neutrophil chemotaxis, and an 8 $\mu$m-pore filter for mononuclear leukocyte chemotaxis; the filters separated the cells from the chemotactic factors contained in the lower compartment in 1 ml. of Medium 199 -ovalbumin. After a 2-½ to 3 hour incubation at 37° C., the filters were removed, fixed and stained. Leukocytes which migrated into the filters were counted microscopically in ten high power fields (hpf), 5 from each of duplicate filters, at a fixed depth in the range of 50–90 $\mu$m from the cell source. The counting depth was selected to achieve a background count of 2–8 leukocytes/hpf in the absence of chemotactic stimulation, and the chemotactic responses were expressed as the net leukocytes/hpf after correction for the background counts. The loss of chemotactic responsiveness of leukocytes pretreated with a chemotactic agent for 30 minutes at 25° C. was expressed as $$\% \text{ deactivation} = \left(1 - \frac{\text{chemotaxis after deactivation}}{\text{chemotaxis of untreated cells}} \times 100\right) (8).$$

EXAMPLE 6

Preparation and Chemotactic Assay of Hydrophobic and Aromatic Analogues of ECF-A Solid phase peptides synthesis methods outlined above have been employed to prepare other tetrapeptides of prototype formula:

$$X^1\text{-Gly-Ser-Glu} \qquad\qquad IV$$

Two of the analogues, namely Leu-Gly-Ser-Glu and Phe-Gly-Ser-Glu, after purification on Sephadex G-10 and Dowex-1 as detailed above possess chemotactic and deactivating activities for human eosinophils in vitro.

EXAMPLE 7

In vivo Chemotactic Activity of Alanyl- and Valyl-Tetrapeptides

The intraperitoneal injection of a single dose of 0.01 –1.0 nmole of either tetrapeptide into rats or guinea pigs resulted in an influx of eosinophils into the peritoneal cavity. Peritoneal eosinophil counts were elevated to levels of two to ten times those of animals injected with only the diluent, Hanks' balanced salt solution, and reached peak levels by 2 –12 hours after the initial injection. Eosinophil counts were still elevated above those of control or normal animals at 24 –48 hours after the dose of peptide. A rise in peritoneal neutrophil counts was appreciated 1 –4 hours after the peak response in eosinophils in the injected guinea pigs. Thus the alanyl- or valyl-tetrapeptides can produce in vivo a local exudate, the cellular composition of which reflects both the nature of the available cell pool and the preferential eosinophil chemotactic activity of the tetrapeptides.

EXAMPLE 8

| | Parenteral Formulations |
|---|---|
| Single dose lyophilized vial | 30 $\mu$g. tetrapeptide<br>1.8 mg. methyl paraben<br>0.2 mg. propyl paraben<br>9.0 mg. sodium chloride |

A solution of the above compounds in 1 ml. of distilled water is bacteriologically filtered aseptically filled into a sterile 5 ml. glass vial and lyophilized. The vial is then capped with a sterile stopper and capped with an aluminum seal. Prior to administration, one ml. of sterile water for injection is added via a sterile hypodermic syringe to redissolve the contents.

| Ready to use solution | |
|---|---|
| | 30 $\mu$g. tetrapeptide<br>5 mg. phenol<br>9 mg. sodium chloride<br>2 mg. sodium acetate |

The above compounds are dissolved in 1 ml. of sterile water for injection.

EXAMPLE 9

Aerosol Formulation (Per Dose)

A total of 3.0 $\mu$g./dose of micronized* tetrapeptide is suspended in 0.04 ml./dose of a vehicle consisting of a surfactant such as sorbitan trioleate (Span 80) dissolved in a fluorochlorohydrocarbon propellant (Freon 11, Freon 12 or mixtures thereof) and the total amount of suspension is added to an aerosol dispenser in an amount to provide the desired number of doses.

*micronized to an average particle size below 20 microns, preferably below 10 microns.

We claim:

1. A tetrapeptide of the formula

Val-Gly-Ser-Glu essentially free of other biogenic peptides and histamine and pharmaceutically acceptable salts thereof.

2. A tetrapeptide of the formula

Ala-Gly-Ser-Glu essentially free of other bioganic peptides and histamine and pharmaceutically acceptable salts thereof.

3. A tetrapeptide of the formula

X-Gly-Ser-Glu wherein X is selected from the group consisting of

| Ile- | Phe- |
| Tyr- | Hexanoyl- |
| Cys- | Valeryl- |
| Met- | Isovaleryl- |
| N-formyl Met- | Caproyl- |
| Try- | Isocaproyl- |
| Leu- | | and pharmaceutically acceptable salts thereof.

4. A compound of claim 3 wherein X is Leu-.
5. A compound of claim 3 wherein X is Phe-.
6. A compound of the formula Y—$X^1$—Gly—Ser($OR^1$)—Glu($OR^2$)—® wherein $X^1$ is Val, Ala, or X where X is selected from the group consisting of

| Ile- | Phe- |
| Tyr- | Hexanoyl- |
| Cys- | Valeryl- |
| Met- | Isovaleryl- |
| N-formyl Met- | Caproyl- |
| Try- | Isocaproyl- |
| Leu- | |

$R^1$ and $R^2$ each independently is selected from benzyl and nitrobenzyl; Y is a solid phase peptide synthesis N-terminal amino protecting group and ® is a resin employed in a solid phase peptide synthesis.

7. The compound of claim 6 wherein Y is t-butyloxycarbonyl and ® is copolystyrene-divinyl benzene.
8. The compound of claim 7 wherein $X^1$ is Val.
9. The compound of claim 7 wherein $X^1$ is Ala.

* * * * *

UNITED STATES PATENT AND TRADEMARK OFFICE
CERTIFICATE OF CORRECTION

PATENT NO. : 4,021,387

DATED : May 3, 1977

INVENTOR(S) : Edward J. Goetzl and K. Frank Austen

It is certified that error appears in the above-identified patent and that said Letters Patent are hereby corrected as shown below:

Col. 2, line 34, "bromoethyl" should be --bromomethyl--;

Col. 2, line 58, "includes" should be --include--;

Col. 3, line 49, "know" should be --known--;

Col. 3, line 68, "0,6-0.7" should be --0.6-0.7--;

Col. 4, line 7, "chromatography" is misspelled;

Col. 5, line 35, "34 ml." should be --3-4 ml.--;

Col. 6, line 21, "amino" should be --Amino--;

Col. 6, line 38, "twodimensional" should be --two-dimensional--;

Col. 7, line 29, after "amino", delete "and";

Col. 7, line 50, "$CH_2C_2$" should be --$CH_2Cl_2$--;

Col. 8, line 28, delete "the";

UNITED STATES PATENT OFFICE
CERTIFICATE OF CORRECTION

Patent No. 4,021,387  Dated May 3, 1977

Inventor(s) Edward J. Goetzl and K. Frank Austen

It is certified that error appears in the above-identified patent and that said Letters Patent are hereby corrected as shown below:

Col. 9, line 18, after "of", insert -- a --.

Signed and Sealed this ninth Day of August 1977

[SEAL]

Attest:

RUTH C. MASON
Attesting Officer

C. MARSHALL DANN
Commissioner of Patents and Trademarks